United States Patent

Higler et al.

[11] Patent Number: 5,919,431
[45] Date of Patent: Jul. 6, 1999

[54] 1,4,7,10-TETRAAZACYCLODODECANE DERIVATIVES, THEIR USE, PHARMACEUTICAL AGENTS CONTAINING THESE COMPOUNDS AND PROCESS FOR THEIR PRODUCTION

[75] Inventors: Christoph-Stephan Higler; Wolfgang Ebert; Mary Lee-Vaupel; Johannes Platzek; Jurgen Conrad; Bernd Raduchel, all of Berlin, Germany

[73] Assignee: Schering Aktiengesellschaft, Germany

[21] Appl. No.: 08/649,672

[22] PCT Filed: Nov. 10, 1994

[86] PCT No.: PCT/EP94/03718

§ 371 Date: Dec. 6, 1996

§ 102(e) Date: Dec. 6, 1996

[87] PCT Pub. No.: WO95/14678

PCT Pub. Date: Jun. 1, 1995

[30] Foreign Application Priority Data

Nov. 24, 1993 [DE] Germany ............... 43 40 809

[51] Int. Cl.⁶ ............ C07D 257/02; A61K 49/00; A61B 5/055
[52] U.S. Cl. .............. 424/9.363; 514/184; 514/836; 540/474; 540/541; 534/14; 534/15; 534/16
[58] Field of Search .................... 540/450, 470, 540/474; 514/184, 836; 424/9.363; 534/14, 15, 16

[56] References Cited

U.S. PATENT DOCUMENTS 5,631,368  5/1997  Schultze et al. ................ 540/474

OTHER PUBLICATIONS

Pulukkody et al. J. Chem. Soc., Perkin Trans 2., 1993., No. 4., pp. 605–620.

Primary Examiner—Mukund J. Shah
Assistant Examiner—Pavanaram K. Sripada
Attorney, Agent, or Firm—Millen, White, Zelano, & Branigan, P.C.

[57] ABSTRACT

The invention relates to new 1,4,7,10-tetraazacyclododecane derivatives of formula I

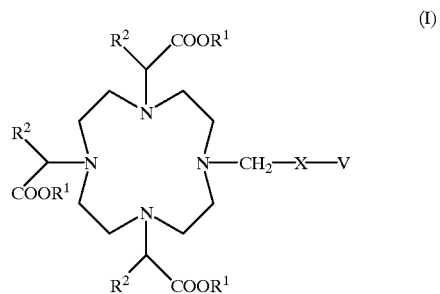

in which $R^1$, $R^2$, X and V have various meanings, their metal complexes, pharmaceutical agents containing these compounds, their use in diagnosis and treatment as well as process for the production of these compounds and agents.

16 Claims, No Drawings

1,4,7,10-TETRAAZACYCLODODECANE DERIVATIVES, THEIR USE, PHARMACEUTICAL AGENTS CONTAINING THESE COMPOUNDS AND PROCESS FOR THEIR PRODUCTION

This application is a 371 of PCT/EP94/03718 filed Nov. 10, 1994.

The invention relates to the object characterized in the claims, i.e., new 1,4,7,10-tetraazacyclododecane derivatives, their metal complexes, pharmaceutical agents containing these compounds, their use in diagnosis and treatment as well as process for the production of these compounds and agents.

In diagnosis and radiotherapy, metal complexes have already been used for some time to supply otherwise toxic metals to the body. Representatives of these metal complexes or complexing agents or their precursors are described, for example, in EP-A 0 545 511, EP-A 0 071 564, 0 255 471, 0 448 191 and in DE-A 34 01 052. The metal complexes described there are distinguished partly already by good compatibility. The described chelates partly can also be dosed higher, which is advantageous especially for the detection of certain diseases outside the central nervous system with the help of nuclear spin tomography (NMR diagnosis), but quite especially in the use of chelates as x-ray contrast media.

In comparison to iodinated x-ray contrast media, chelates can offer the advantage that they show radiation absorption in the higher-energy range and thus result in a reduction of the radiation exposure for the patient. This also results in an improvement of the requirements for the energy subtraction method. A further advantage is the avoidance of contrast media reactions, such as, e.g., the so-called allergy-like or cardiovascular side effects.

In addition to open-chain ligands, cyclic chelating agents are also used as complexing agents. WO 91/08272 thus discloses macrocycles that contain heteroatoms as well as their use as additives to liquid crystal mixtures.

WO 93/02045 describes, i.a., tetraazamacrocycles with aminomethylene sulfo groups that are subject to the risk of thermal decomposition in the case of heat sterilization. This is true in the same way for the macrocycles that contain N-methylenesulfonate groups described in WO 93/12097. Also, the $SO_3$ group contained in these compounds is largely unsuitable for complexing metal ions such as, e.g., gadolinium.

The chelates are to meet the following requirements:

High concentration of radiation-absorbing elements in the solution or strong influencing of the NMR signals;
a pharmacokinetics suitable for diagnosis;
permanent bond of the metal ions in complexes that can be separated even under in vivo conditions;
good compatibility of the highly-concentrated, large-dose complex solution or suspension;
low allergoid potential of all components of the contrast medium;
high stability and shelf life of the chemical components of the contrast medium solution or suspension.

These requirements apply to a varying extent and in a varying way, but basically to all uses of the above-mentioned complexes in in-vivo diagnosis as well as partially in radiotherapy.

New complexing agents or complexes of the above-described type, which are to be improved with respect to the basic hydrophilia, i.e., in their water-solubility and with respect to their compatibility in the organism, are the object of this invention.

This object is achieved with the 1,4,7,10-tetraazacyclododecane derivatives according to claim 1.

The latter are 1,4,7,10-tetraazacyclododecane derivatives of general formula I

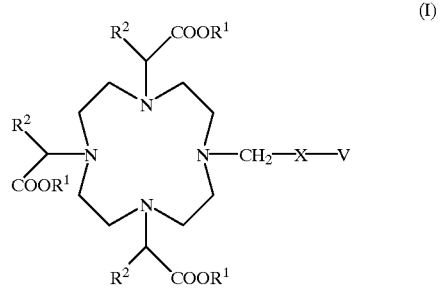

in which
  $R^1$, independently of one another, stand for H, a $C_1$–$C_6$ alkyl radical or a metal ion equivalent,
  $R^2$, independently of one another, stand for H, a methyl or ethyl radical,
  X stands for a direct bond or a $C_1$–$C_{10}$ alkylene group or a $C_2$–$C_{23}$ alkylene group interrupted by one or more oxygen atoms,
whereby the alkyl radicals and alkylene groups are substituted optionally by one or more hydroxy radicals and/or lower alkoxy radicals and/or contain one or more carbonyl functions, and
  V means a radical of formula II

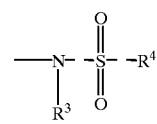

in which
  $R^3$ stands for a hydrogen atom, for a saturated, unsaturated, straight-chain or branched-chain alkyl, aryl or aralkyl radical or cyclic hydrocarbon radical with up to 40 carbon atoms,
  $R^4$ has the meaning indicated for $R^3$ with the exception of hydrogen
or
  $R^3$ and $R^4$ together with the adjacent sulfur and nitrogen atoms represent a saturated 5- or 6-ring optionally containing another heteroatom,
whereby $R^3$ and/or $R^4$ optionally have one or more carbonyl functions and/or are interrupted by one or more oxygen atoms and/or by one or more >N—$CH_2$—$COOR^1$ groups and/or are substituted by one or more O═C═N—, S═C═N groups, or hydroxy, alkoxy, carboxylato, carbonyl, —CHO, halogen, amido or amino radicals, whereby the hydroxy groups are present in free or protected form.

These substances and the solutions prepared from them meet the requirements to be set for pharmaceutically usable chelates. They have an effectiveness that is strong and can be matched by the selection of suitable metal atoms to the respective principles of the diagnostic or therapeutic method (x-ray, NMR, nuclear medicine).

The substances according to the invention can be used:

1. For NMR diagnosis in the form of their complexes with a paramagnetic metal ion. These are especially the divalent and trivalent ions of the elements of atomic numbers 21 to 29, 42, 44 and 58 to 70. Suitable ions are, for example, the chromium(III), manganese(II), iron(II), cobalt(II), nickel (II), copper(II), praseodymium(III), neodymium(III), samarium(III) and ytterbium(III) ion. Because of their very strong magnetic moment, the gadolinium(III), terbium(III), dysprosium(III), holmium(III), erbium(III) and the iron(III) ions are especially preferred.

2. For the use of the agent according to the invention in nuclear medicine, a radioactive metal ion is selected. Suitable are, e.g., radioisotopes of the elements copper, cobalt, gallium, germanium, yttrium, strontium, technetium, indium, ytterbium, gadolinium and samarium.

3. If the means according to the invention is intended for use in x-ray diagnosis, especially metal ions of elements of higher atomic numbers are suitable to achieve a sufficient absorption of the x rays. Metal ions of the elements of atomic numbers 21 to 29, 31, 32, 38, 39, 42 to 44, 57 to 83 have been found suitable; these are, for example, the lanthanum(III) ion and the above-mentioned ions of the lanthanide series.

Even without specific measures, the pharmacokinetics of the compounds according to the invention allows the improvement of the diagnosis of numerous diseases. The complexes are unchanged for the most part and are quickly precipitated again, so that despite high dosage, the organism is not unnecessarily stressed.

Surprisingly, the metal complexes according to the invention show an excellent water solubility with simultaneously great lipophilia. Thus, the latter is comparable with that observed in the case of 1-alkyl-4,7,10-tris-(carboxylatomethyl)-1,4,7,10-tetraazacyclododecane complexes (EP 0 255 471), but the alkyl derivatives show a poorer water solubility.

The compounds according to the invention have a very good chemical stability and can be altered within wide ranges especially on the heterocycle with respect to their complexing properties and on the sulfonamide radical with respect to the basic hydrophilia and the compatibility in the organism and can be matched to desired conditions. In addition to the metal ion, the properties can be altered to the requirements of effectiveness, pharmacokinetics, compatibility, manageability, etc. by the selection of the sulfonamide radical and/or by the selection of salt formers. Thus, a specificity of the compound that is very desirable in diagnosis and treatment for structures in the organism can be achieved for certain biochemical substances, for metabolic processes, for states of the tissues or bodily fluids, e.g., by the inclusion of biological substances, which exhibit an interaction with biological systems. Thus, the tetraazacyclododecane derivative according to the invention can be coupled, e.g., with amino acids, peptides or other biomolecules or a polymer, whereby the specific distribution in the body can be changed by these substances. The use of such principles is all the more possible the more sensitive the detection process for a diagnostic agent is or the more effective a, e.g., radiolabeled complex in the treatment is.

The compounds according to the invention can be used in the form of their complexes with radioisotopes, such as, e.g., $^{192}$Ir, also in radiotherapy.

If the compounds of general formula I according to the invention contain positron-emitting isotopes, such as, e.g., Sc-43, Sc-44, Fe-52, Co-55, Ga-68 or Cu-61, they can be used in positron emission tomography (PET).

If the compounds of general formula I according to the invention contain isotopes that emit γ-radiation, such as, e.g., Tc-99 m or In-111, they can be used in single-photon emission tomography (SPECT).

If the compounds of general formula I according to the invention contain isotopes that emit α-particles, such as, e.g., Bi-211, Bi-212, Bi-213, Bi-214, At-209, At-211 or β-emitting isotopes, such as, e.g., Sc-47, Sc-48, Ga-72, Y-90, Re-186 or Re-188, they can be used in radiotherapy.

Compounds of general formula I with two $R^1$ meaning hydrogen are designated as complexing agents and with at least two of substituents $R^1$ meaning a metal ion equivalent as metal complexes.

If not all acidic hydrogen atoms are substituted by the diagnostically or therapeutically effective metal ion, the remaining hydrogen atoms (or the remaining hydrogen atom) can be replaced by cations of inorganic and/or organic bases or amino acids. Suitable inorganic cations are, for example, the lithium ion, calcium ion, potassium ion, magnesium ion and especially the sodium ion. Suitable cations of organic bases are, i.a., those of primary, secondary or tertiary amines, such as, e.g., ethanolamine, diethanolamine, morpholine, glucamine, N,N-dimethylglucamine and especially N-methylglucamine.

Suitable cations of amino acids are, for example, those of lysine, arginine, and ornithine.

Examples for $R^3$ are especially the hydrogen atom, a straight-chain or branched-chain $C_4$–$C_{18}$ alkyl radical, $CH_3$—O—$(CH_2)_2$—, $C_6H_5$—$CH_2$—, $C_6H_5$—$(CH_2)_2$—, $C_6H_5$—$CH_2$—O—$(CH_2)_2$—, $CH_3$—O—$C_6H_4$—$(CH_2)_2$—,

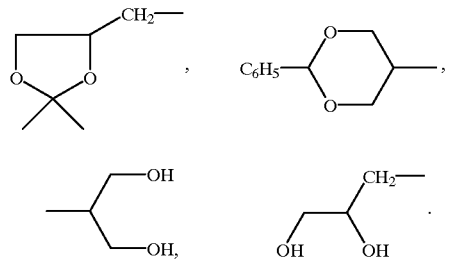

Examples for $R^4$ are especially a straight-chain or branched $C_1$–$C_{18}$, alkyl radical or a $CH_3$—$C_6H_4$—, $C_6H_5$—, $O_2N$—$C_6H_4$—, $H_2N$—$C_6H_4$—, O=C=N—$C_6H_4$—, S=C=N—$C_6H_4$ radical.

Especially preferred are compounds of general formula I, in which X is a $C_2$–$C_5$ alkylene group, advantageously with at least one hydroxy radical, especially a hydroxy radical in β-position to the tetraazacyclododecane ring. It is especially preferred in this case if -X-V stands for

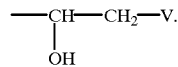

These compounds can be very easily produced as described below, are chemically stable, nontoxic, and contribute especially to a large basic hydrophilia.

Further, in the compounds of general formula I according to the invention, the following radicals or groups individually or in combination are especially preferred:

$R^1$: ⅓ $Gd^{3+}$ and thus NMR diagnosis $R^2$: H, since these compounds are especially simple to produce, have a good basic hydrophilia and exhibit high stability and result in very stable metal complexes;

$R^3$: $C_1$–$C_{16}$ alkyl radical, phenyl-$C_1$–$C_4$ alkyl radical especially with phenyl in omega-position;

R4: $C_1$–$C_6$ alkyl radical, especially the methyl radical.

All saturated, unsaturated, aromatic or cyclic hydrocarbon radicals or groups, also those with heteroatoms in the chain or in the ring, can be unbranched, branched, conjugated and in the case of cyclic compounds, can also have alkyl radicals, preferably lower alkyl radicals, and cyclic radicals, which all also can contain the indicated substituents. Cyclic radicals or groups can optionally be bound to the molecule (the heteroatoms), i.e., directly or by a (preferably lower) alkylene group (also cyclic) or aromatic group, all of which can be interrupted also by one or more heteroatoms. Lower alkyl radicals are those up to $C_6$, preferably up to $C_4$. Nitrogen-containing radicals (e.g., amino or amido) can also have the indicated substituents, such as, e.g., alkyl radicals, as part of the radical value (e.g., 40 C-atoms).

Halogen means Cl, Br, I and especially F. The indication of metals in principle includes radionuclides.

The compounds of general formula I according to the invention are suitable especially for the production of pharmaceutical agents. These pharmaceutical agents according to the invention contain at least one metal complex of general formula I with at least two radicals $R^1$ meaning a metal ion equivalent as well optionally in addition the metal-free complexing agent in the form of its calcium salt.

The production of the pharmaceutical agents according to the invention, which contain at least one metal complex or complexing agent of general formula I with at least two radicals $R^1$ meaning a metal ion equivalent, takes place in a way known in the art, by the complex compounds according to the invention as well as optionally the metal-free complexing agent in the form of its salt being suspended or dissolved in aqueous medium—optionally by adding the additives that are commonly used in galenicals and optionally by adding additional active ingredients—and then the suspension or solution optionally being sterilized. Suitable additives are, for example, physiologically harmless buffers (such as, e.g., trimethamine), small additions of other complexing agents (such as, e.g., diethylenetriaminepentaacetic acid), if necessary, electrolytes, such as, e.g., sodium chloride, and, if necessary, antioxidants, such as, e.g., ascorbic acid.

If suspensions or solutions of the agents according to the invention in water or physiological salt solution are desired for enteral administration or other purposes, they are mixed with one or more adjuvants that are commonly used in galenicals (e.g., methyl cellulose, lactose, mannitol) and/or surfactants (e.g., lecithins, Twin®, MYRJ® and/or aromatic substances for taste correction (e.g., ethereal oils).

In principle, it is also possible to produce the pharmaceutical agents according to the invention even without isolating the complexes, in each case care must especially be used to undertake the chelation so that the salts and salt solutions according to the invention are practically free of noncomplexed metal ions that have a toxic effect. This can be ensured, for example, with the help of color indicators, such as xylenol orange, by control titration during the production process. The invention therefore relates also to the process for the production of complex compounds and their salts. A purification of the isolated complex remains as a last safety measure.

The pharmaceutical agents according to the invention contain preferably 0.1 mmol to 2 mol/l of the compound of general formula I with $R^1$ equal to H and/or a metal ion equivalent and are generally dosed in amounts of 0.1 μmol–5 mmol/kg. They are intended for enteral and parenteral administration.

The agents according to the invention fulfill especially the varied requirements for suitability as contrast media for the nuclear spin tomography. After oral or parental administration by increasing the signal intensity, they are thus excellently suited to improve the image, obtained with the help of the nuclear spin tomograph, in its informative value. Further, they show the high effectiveness, which is necessary to load the body with the smallest possible amounts of foreign substances and the good compatibility, which is necessary to maintain the noninvasive nature of the examinations.

The good water-solubility of the agents according to the invention makes it possible to produce highly-concentrated solutions, by which the dilution of the bodily fluid is kept within limits. In addition, the agents according to the invention exhibit a high stability in vivo as in vitro, whereby a release or an exchange of the ions bound in the complexes within the retention time of the complex in the organism can be practically disregarded. Other application references and further literature can be found in EP-A-0 255 471, especially pages 36–38.

As it turned out with this invention, based on their advantageous profile image, sulfonamide radicals, especially N-substituted sulfonamide radicals, in at least divalent metal complex compounds or in (chelate) compounds that are suitable for the production of such metal complex compounds are especially suitable for the production of an agent for NMR diagnosis, diagnostic radiology or radiodiagnosis or radiotherapy. The invention thus relates also to this use of such sulfonamide radicals. Especially advantageous are sulfonamide radicals of general formula II

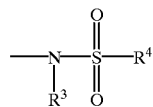

(II)

which are bound to the complexing agent, optionally by a bridgetype crosslink, whereby $R^3$ stands for a hydrogen atom, for a saturated, unsaturated, straight-chain or branched-chain alkyl, aryl or aralkyl radical or a cyclic hydrocarbon radical with up to 40 carbon atoms, $R^4$ which has the meaning indicated for $R^3$ with the exception of hydrogen or $R^3$ and $R^4$ together with the adjacent sulfur and nitrogen atoms represent a saturated 5- or 6-ring optionally containing another heteroatom, whereby $R^3$ and/or $R^4$ optionally have one or more carbonyl functions and/or are interrupted by one or more oxygen atoms and/or by one or more >N—$CH_2$—$COOR^1$ groups and/or are substituted by one or more O=C=N—, S=C=N— groups or hydroxy, alkoxy, carboxylato, carbonyl, —CHO, halogen, amido or amino radicals, whereby the hydroxy groups are present in free or protected form.

The invention relates especially to the use of the described sulfonamide radicals in (complex) compounds of general formula I.

The compounds according to the invention can easily be obtained, e.g., by reacting a tetraazatricyclotridecane, which can be obtained according to methods known in the literature (U.S. Pat. No. 4,085,106 or 4,130,715) from the corresponding 1,4,7,10-tetraazacyclododecane by reaction with dimethylformamide dimethyl acetal, with an N-(epoxyalkyl)-sulfonic acid amide, followed by a saponification of the alkoxy radicals, alkylation with α-haloacetic ester, subsequent ester cleavage as well as final introduction of the respective metal ion by reaction with the corresponding metal salt or metal oxide. The N-(epoxyalkyl)-sulfonic acid amide can advantageously be produced by epoxy alkylation of an N-substituted sulfonic acid amide of general formula IIa

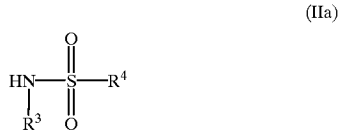

(IIa)

in which $R^3$ and $R^4$ have the above meaning. Especially advantageous here is the production of the N-substituted N-[(2-oxiranyl)-methyl]-sulfonic acid amides, since the latter are easy to obtain from the corresponding N-substituted sulfonic acid amides by reaction with epichlorohydrin.

The corresponding N-substituted sulfonic acid amides can again by obtained by reacting a corresponding sulfonic acid chloride with a corresponding primary amine.

The following examples are used for a more detailed explanation of the object of the invention, without intending that they be limited to this object.

EXAMPLE 1a–k

Production of N-substituted sulfonic acid amides 100 mmol of the respective amine (a–k; see FIG. 1) is dissolved in 500 ml of absolute dichloromethane and mixed with 100 mmol of triethylamine. 100 mmol of the respective sulfonic acid chloride (a–k), dissolved in 250 ml of absolute dichloromethane, is instilled at 0° C. under nitrogen atmosphere. Then, it is stirred for 1 hour at 0° C. and stirred for 14 more hours at room temperature. For working-up, it is shaken three times with 5% citric acid, three times with saturated, aqueous sodium bicarbonate solution and three times with water. After the dichloromethane phase is dried on sodium sulfate, it is concentrated by evaporation in a vacuum. The thus resulting crude sulfonamides are purified by crystallization from diethyl ether/n-hexane or distillation on a bulb tube. Colorless to slightly yellowish oils or white powders are obtained. The individual results are represented in FIG. 1.

EXAMPLE 1l

N-((3-,3-Dimethyl-2,4-dioxa-cyclopentyl)-methyl)-methanesulfonic acid amide 45.56 g (500 mmol) of 2,3-dihydroxypropylamine is introduced in 1000 ml of dimethylformamide. After 50.6 g (500 mmol) of triethylamine is added, 57.28 g (500 mmol) of methanesulfonic acid chloride, dissolved in 500 ml of dichloromethane, is instilled under nitrogen atmosphere at 0° C. Then, it is stirred for 1 hour at 0° C. and for 16 hours at room temperature. After the reaction (TLC control) is completed, it is filtered, and the filtrate is concentrated by evaporation in a vacuum. The residue is mixed with 500 ml of tetrahydrofuran, cooled to 0° C. and again filtered. The filtrate is mixed with 500 ml of tetrahydrofuran, 260 ml of 2,2-dimethoxypropane and 5.2 g of ammonium chloride. The resulting reaction mixture is refluxed for 4 hours, then the solvent is evaporated in a vacuum and the residue is taken up in dichloromethane. It is washed three times with one-percent aqueous citric acid, three times with saturated, aqueous sodium bicarbonate solution and finally three times with water. After the organic phase is dried on sodium sulfate, the solvent is drawn off in a vacuum and the residue is distilled on a bulb tube.

Yield: 46.46 g (44.4%), yellowish oil.

EXAMPLE 1m

N-((Dioxa-4-phenyl-cyclohexyl)-methyl)-methanesulfonic acid amide 45.56 g (500 mmol) of serinol is introduced in 1l of absolute dimethylformamide. After 50.6 g (500 mmol) of triethylamine is added, 57.28 g (500 mmol) of methanesulfonic acid chloride, dissolved in 500 ml of absolute dichloromethane, is instilled under nitrogen atmosphere at 0° C. Then, it is stirred for 1 hour at 0° C. and for 16 hours at room temperature.

After the reaction (TLC control) is completed, it is filtered and the filtrate is concentrated by evaporation in a vacuum. The residue is mixed with 500 ml of tetrahydrofuran, cooled to 0° C. and again filtered. The filtrate is mixed with 500 ml of tetrahydrofuran, 250 ml of benzaldehyde dimethyl acetate and 5.2 g of ammonium chloride. The resulting reaction mixture is refluxed for 5 hours, then the solvent is evaporated in a vacuum and the residue is taken up in dichloromethane. It is washed three times with one-percent aqueous citric acid, three times with saturated, aqueous sodium bicarbonate solution and then three times with water. After the organic phase is dried on sodium sulfate, the solvent is drawn off in a vacuum and the residue is distilled on a bulb tube.

Yield: 51.46 g (40%), yellowish oil.

EXAMPLE 2

Production of the N-substituted N-((2-oxiranyl)-methyl)-sulfonic acid amides 75 mmol of the sulfonamide produced under Examples 1a to 1m is dissolved in 250 ml of 1,2-dimethoxyethane and mixed under nitrogen atmosphere with 75 mmol of potassium tert-butylate. It is stirred for 0.5 hour at room temperature, 750 mmol of epichlorohydrin is added and the resulting reaction mixture is refluxed for 0.5 hour. After the reaction (TLC control) is completed, it is concentrated by evaporation in a vacuum and the resulting epoxides are purified by crystallization from n-hexane or distillation on a bulb tube. Colorless to slightly yellowish oils or white powders are obtained. The individual results are represented in FIG. 2.

EXAMPLE 3a

1-[3-(N-Butyl-mesylamino)-2-hydroxypropyl]-4,7,10-tris-(ethoxycarbonylmethyl)-1,4,7,10-tetraazacyclododecane 200 ml of absolute ethanol is poured over 8.61 g (20 mmol) of N,N',N''-tris-(ethoxycarbonylmethyl)-1,4,7,10-tetraazacyclododecane (produced according to DE 36 25 417 A1) in a bomb tube. After 4.15 g (20 mmol) of N-butyl-N-[(2-oxiranyl)-methyl]-methanesulfonic acid amide is added (Example 2a), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (eluent: chloroform/methanol; methanol: 0–80%).

Yield: 7.97 g (62.5%), colorless oil

Analysis: relative to the anhydrous substance Cld: C 52.73 H 8.69 N 10.98 S 5.03 O 22.58 Fnd: C 52.51 H 8.73 N 10.79 S 4.78 O

EXAMPLE 3b

1-[3-(N-Butyl-mesylamino)-2-hydroxypropyl]-4,7,10-tris-(hydroxycarbonylmethyl)-1,4,7,10-tetraazacyclododecane 6.38 g (10 mmol) of the protected ligand produced under Example 3a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml and the resulting solution of the ligand is chromatographed on silica gel RP-18 (eluent: methanol/water; methanol: 0–20%).

Yield: 2.07 g (37.4%), colorless oil

Analysis: Relative to the anhydrous substance Cld: C 47.72 H 7.83 N 12.65 S 5.79 O 26.01 Fnd: C 47.43 H 7.72 N 12.38 S 5.48 O

EXAMPLE 3c

1-[3-(N-Butyl-mesylamino)-2-hydroxypropyl]-4,7,10-tris-(carboxylatomethyl)-1,4,7,10-tetraazacyclododecane gadolinium complex 1.66 g (3 mmol) of the ligand produced under Example 3b is dissolved in 50 ml of water and mixed with 543.7 mg (1.5 mmol) of gadolinium(III) oxide. The resulting suspension is heated for 2 hours with vigorous stirring to 90° C. and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–40%).

Yield: 1.32 g (62.2%), white powder

Analysis: Relative to the anhydrous substance Cld: C 37.33 H 5.70 N 9.89 S 4.53 O 20.34 Gd 22.21 Fnd: C 37.15 H 5.91 N 9.82 S 4.24 O Gd 22.03

EXAMPLE 4a

1-[3-(N-Octyl-mesylamino)-2-hydroxypropyl]-4,7,10-tris-(ethoxycarbonylmethyl)-1,4,7,10-tetraazacyclododecane 200 ml of absolute ethanol is poured over 8.61 g (20 mmol) of N,N',N"-tris-(ethoxycarbonylmethyl)-1,4,7,10-tetraazacyclododecane (produced according to DE 36 25 417 A1) in a bomb tube. After 5.27 g (20 mmol) of N-octyl-N-[(2-oxiranyl)-methyl]-methanesulfonic acid amide is added (Example 2b), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (eluent: chloroform/methanol; methanol: 0–80%).

Yield: 7.25 g (52.2%), colorless oil

Analysis: Relative to the anhydrous substance Cld: C 55.39 H 9.15 N 10.09 S 4.62 O 20.75 Fnd: C 55.12 H 8.93 N 9.88 S 4.37 O

EXAMPLE 4b

1-[3-(N-Octyl-mesylamino)-2-hydroxypropyl]-4,7,10-tris-(hydroxycarbonylmethyl)-1,4,7,10-tetraazacyclododecane 6.94 g (10 mmol) of the protected ligand produced under Example 4a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml, and the resulting solution of the ligand is chromatographed on silica gel RP-18 (eluent: methanol/water; methanol: 0–20%).

Yield: 2.17 g (35.6%), colorless oil

Analysis: Relative to the anhydrous substance Cld: C 51.21 H 8.43 N 11.49 S 5.26 O 23.61 Fnd: C 50.93 H 8.53 N 11.19 S 5.13 O

EXAMPLE 4c

1-[3-(N-Octyl-mesylamino)-2-hydroxypropyl]-4,7,10-tris-(carboxylatomethyl)-1,4,7,10-tetraazacyclododecane gadolinium complex 1.83 g (3 mmol) of the ligand produced under Example 4b is dissolved in 50 ml of water and mixed with 543.7 mg (1.5 mmol) of gadolinium(III) oxide. The resulting suspension is heated for 2 hours with vigorous stirring to 90° C., and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–40%).

Yield: 1.53 g (66.8%), white powder

Analysis: Relative to the anhydrous substance Cld: C 40.87 H 6.33 N 9.17 S 4.20 O 18.85 Gd 20.58 Fnd: C 40.62 H 6.57 N 9.02 S 4.05 O Gd 20.29

EXAMPLE 5a

1-[3-(N-Undecyl-mesylamino)-2-hydroxypropyl]-4,7,10-tris-(ethoxycarbonylmethyl)-1,4,7,10-tetraazacyclododecane 200 ml of absolute ethanol is poured over 8.61 g (20 mmol) of N,N',N"-tris-(ethoxycarbonylmethyl)-1,4,7,10-tetraazacyclododecane (produced according to DE 36 25 417 A1) in a bomb tube. After 6.11 g (20 mmol) of N-undecyl-N-[(2-oxiranyl)-methyl]-methanesulfonic acid amide is added (Example 2c), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (eluent: chloroform/methanol; methanol: 0–80%).

Yield: 7.89 g (53.6%), colorless oil

Analysis: Relative to the anhydrous substance Cld: C 57.11 H 9.45 N 9.52 S 4.36 O 19.56 Fnd: C 56.97 H 9.18 N 9.43 S 4.19 O

EXAMPLE 5b

1-[3-(N-Undecyl-mesylamino)-2-hydroxypropyl]-4,7,10-tris-(hydroxycarbonylmethyl)-1,4,7,10-tetraazacyclododecane 7.36 g (10 mmol) of the protected ligand produced under Example 5a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml and the resulting solution of the ligand is chromatographed on silica gel RP-18 (eluent: methanol/water; methanol: 0–20%).

Yield: 2.13 g (32.7%), colorless oil

Analysis: Relative to the anhydrous substance Cld: C 53.43 H 8.81 N 10.74 S 4.92 O 22.09 Fnd: C 53.27 H 8.93 N 10.46 S 4.70 O

EXAMPLE 5c

1-[3-(N-Undecyl-mesylamino)-2-hydroxypropyl]-4,7,10-tris-(carboxylatomethyl)-1,4,7,10-tetraazacyclododecane gadolinium complex 1.96 g (3 mmol) of the ligand produced under Example 5b is dissolved in 50 ml of water and mixed with 543.7 mg (1.5 mmol) of gadolinium(III) oxide. The resulting suspension is heated for 2 hours with vigorous stirring to 90° C. and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–40%).

Yield: 1.18 g (48.8%), white powder

Analysis: Relative to the anhydrous substance Cld: C 43.21 H 6.75 N 8.69 S 3.98 O 17.86 Gd 19.51 Fnd: C 43.18 H 6.92 N 8.63 S 3.69 O Gd 19.40

EXAMPLE 6a

1-[3-(N-2-Methoxyethyl-mesylamino)-2-hydroxypropyl]-4,7,10-tris-(ethoxycarbonylmethyl)-1,4,7,10-tetraazacyclododecane 200 ml of absolute ethanol is poured over 8.61 g (20 mmol) of N,N',N''-tris-(ethoxycarbonylmethyl)-1,4,7,10-tetraazacyclododecane (produced according to DE 36 25 417 A1) in a bomb tube. After 4.19 g (20 mmol) of N-(2-methoxyethyl)-N-[(2-oxiranyl)-methyl]-methanesulfonic acid amide is added (Example 2d), the bomb tube is closed, flushed with nitrogen, and the resulting reaction mixture is heated for 16 hours to 90° C. After the reaction (TLC control) is completed, the solvent is evaporated in a vacuum, and the yellowish, oily residue is chromatographed on silica gel (eluent: chloroform/methanol; methanol: 0–80%).

Yield: 7.35 g (57.4%), colorless oil

Analysis: Relative to the anhydrous substance Cld: C 50.69 H 8.35 N 10.95 S 5.01 O 25.01 Fnd: C 50.42 H 8.07 N 10.81 S 4.79 O

EXAMPLE 6b

1-[3-(N-2-Methoxyethyl-mesylamino)-2-hydroxypropyl]-4,7,10-tris-(hydroxycarbonylmethyl)-1,4,7,10-tetraazacyclododecane 6.40 g (10 mmol) of the protected ligand produced under Example 6a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml and the resulting solution of the ligand is chromatographed on silica gel RP-18 (eluent: methanol/water; methanol: 0–20%).

Yield: 2.22 g (39.9%), colorless oil

Analysis: Relative to the anhydrous substance Cld: C 45.39 H 7.44 N 12.60 S 5.77 O 28.79 Fnd: C 45.11 H 7.58 N 12.41 S 5.48 O

EXAMPLE 6c

1-[3-(N-2-Methoxyethyl-mesylamino)-2-hydroxypropyl]-4,7,10-tris-(carboxylatomethyl)-1,4,7,10-tetraazacyclododecane gadolinium complex 1.67 g (3 mmol) of the ligand produced under Example 6b is dissolved in 50 ml of water and mixed with 543.7 mg (1.5 mmol) of gadolinium(III) oxide. The resulting suspension is heated for 2 hours with vigorous stirring to 90° C., and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–40%).

Yield: 1.37 g (64.3%), white powder

Analysis: Relative to the anhydrous substance Cld: C 35.53 H 5.40 N 9.87 S 4.52 O 22.54 Gd 22.15 Fnd: C 35.48 H 5.67 N 9.69 S 4.33 O Gd 22.12

EXAMPLE 7a

1-[3-(N-Benzyl-mesylamino)-2-hydroxypropyl]-4,7,10-tris-(ethoxycarbonylmethyl)-1,4,7,10-tetraazacyclododecane 200 ml of absolute ethanol is poured over 8.61 g (20 mmol) of N,N',N''-tris-(ethoxycarbonylmethyl)-1,4,7,10-tetraazacyclododecane (produced according to DE 36 25 417 A1) in a bomb tube. After 4.83 g (20 mmol) of N-benzyl-N-[(2-oxiranyl)-methyl]-methanesulfonic acid amide is added (Example 2e), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (eluent: chloroform/methanol; methanol: 0–80%).

Yield: 6.93 g (51.6%), colorless oil

Analysis: Relative to the anhydrous substance Cld: C 55.42 H 7.95 N 10.42 S 4.77 O 21.43 Fnd: C 55.31 H 7.72 N 10.37 S 4.48 O

EXAMPLE 7b

1-[3-(N-Benzyl-mesylamino)-2-hydroxypropyl]-4,7,10-tris-(hydroxycarbonylmethyl)-1,4,7,10-tetraazacyclododecane 6.72 g (10 mmol) of the protected ligand produced under Example 7a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml and the resulting solution of the ligand is chromatographed on silica gel RP-18 (eluent: methanol/water; methanol: 0–20%).

Yield: 2.36 g (40.2%), colorless oil

Analysis: Relative to the anhydrous substance Cld: C 51.09 H 7.03 N 11.92 S 5.46 O 24.50 Fnd: C 50.81 H 7.31 N 11.65 S 5.22 O

EXAMPLE 7c

1-[3-(N-Benzyl-mesylamino)-2-hydroxypropyl]-4,7,10-tris-(carboxylatomethyl)-1,4,7,10-tetraazacyclododecane gadolinium complex 1.76 g (3 mmol) of the ligand produced under Example 7b is dissolved in 50 ml of water and mixed with 543.7 mg (1.5 mmol) of gadolinium(III) oxide. The resulting suspension is heated for 2 hours with vigorous stirring to 90° C. and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–40%).

Yield: 1.62 g (72.8%), white powder

Analysis: Relative to the anhydrous substance Cld: C 40.47 H 5.16 N 9.44 S 4.32 O 19.41 Gd 21.19 Fnd: C 40.18 H 5.42 N 9.21 S 4.21 O Gd 20.93

EXAMPLE 7d

1-[3-(Mesylamino)-2-hydroxypropyl]-4,7,10-tris-(carboxylatomethyl)-1,4,7,10-tetraazacyclododecane gadolinium complex 1.48 g (2 mmol) of the complex produced under Example 7c is dissolved in 50 ml of water and mixed with 150 mg of palladium on carbon (10%). It is hydrogenated for 4 hours at 60° C. and 3 atmospheres of hydrogen pressure. After the reaction (TLC control) is completed, it is filtered, concentrated by evaporation to a volume of 10 ml and the complex is purified by chromatography on silica gel RP-18 (eluent: water/tetrahydrofuran; tetrahydrofuran: 0–5%).

Yield: 0.63 g (48.3%), white powder

Analysis: Cld: C 33.17 H 4.95 N 10.74 O 22.09 Gd 24.13 Fnd: C 33.08 H 5.17 N 10.49 O Gd 23.94

EXAMPLE 7e

1-[3-((N-Carboxylatomethyl)-mesylamino)-2-hydroxypropyl]-4,7,10-tris-(carboxylatomethyl)-1,4,7,10-tetraazacyclododecane gadolinium complex 1.3 g (2 mmol) of the complex produced under Example 7d is dissolved in 50 ml of water. It is adjusted to pH =8.5 by adding 2N sodium hydroxide solution and alkylated with 0.945 g (10 mmol) of α-chloroacetic acid. In this case, the reaction medium is kept at pH =8.5 by adding 2N aqueous sodium hydroxide solution in portions. It is stirred overnight at room temperature, brought to pH =4.5 by adding 2N aqueous hydrochloric acid, concentrated by evaporation to 10 ml in a vacuum at room temperature and the complex is purified by chromatography on silica gel RP-18 (eluent: water/tetrahydrofuran; tetrahydrofuran: 0–20%).

Yield: 0.829 g (58.4%) of white powder

Analysis: Relative to the anhydrous substance Cld: C 33.84 H 4.83 N 9.87 S 4.52 O 24.79 Gd 22.15 Fnd: C 33.58 H 5.16 N 9.71 S 4.24 O Gd 19.88

EXAMPLE 8a

1-[3-(N-2-Phenylethyl-mesylamino)-2-hydroxypropyl]-4,7,10-tris-(ethoxycarbonylmethyl)-1,4,7,10-tetraazacyclododecane 200 ml of absolute ethanol is poured over 8.61 g (20 mmol) of N,N',N"-tris-(ethoxycarbonylmethyl)-1,4,7,10-tetraazacyclododecane (produced according to DE 36 25 417 A1) in a bomb tube. After 5.11 g (20 mmol) of N-(2-phenylethyl)-N-[(2-oxiranyl)-methyl]-methanesulfonic acid amide is added (Example 2f), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (Eluent: chloroform/methanol; methanol: 0–80%).

Yield: 6.76 g (49.3%), colorless oil

Analysis: Relative to the anhydrous substance Cld: C 56.04 H 8.08 N 10.21 S 4.68 O 20.99 Fnd: C 55.86 H 7.93 N 10.14 S 4.57 O

EXAMPLE 8b

1-[(3-(N-2-Phenylethyl-mesylamino)-2-hydroxypropyl]-4,7,10-tris-(hydroxycarbonylmethyl)-1,4,7,10-tetraazacyclododecane 6.86 g (10 mmol) of the protected ligand produced under Example 8a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml, and the resulting solution of the ligand is chromatographed on silica gel RP-18 (eluent: methanol/water; methanol: 0–20%).

Yield: 2.46 g (40.9%), colorless oil

Analysis: Relative to the anhydrous substance Cld: C 51.90 H 7.20 N 11.64 S 5.33 O 23.93 Fnd: C 51.65 H 7.38 N 11.42 S 5.12 O

EXAMPLE 8c

1-[3-(N-2-Phenylethyl-mesylamino)-2-hydroxypropyl]-4,7,10-tris-(carboxylatomethyl)-1,4,7,10-tetraazacyclododecane gadolinium complex 1.81 g (3 mmol) of the ligand produced under Example 8b is dissolved in 50 ml of water and mixed with 543.7 mg (1.5 mmol) of gadolinium(III) oxide. The resulting suspension is heated for 2 hours with vigorous stirring to 90° C. and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–40%).

Yield: 1.14 g (50.3%), white powder

Analysis: Relative to the anhydrous substance Cld: C 41.31 H 5.33 N 9.26 S 4.24 O 19.05 Gd 20.80 Fnd: C 41.20 H 5.53 N 9.11 S 4.07 O Gd 20.63

EXAMPLE 9a

1-[3-(N-[2-(4-Methoxyphenyl)-ethyl]-mesylamino)-2-hydroxypropyl]-4,7,10-tris-(ethoxycarbonylmethyl)-1,4,7,10-tetraazacyclododecane 200 ml of absolute ethanol is poured over 8.61 g (20 mmol) of N,N',N"-tris-(ethoxycarbonylmethyl)-1,4,7,10-tetraazacyclododecane (produced according to DE 36 25

417 A1) in a bomb tube. After 5.71 g (20 mmol) of N-(2-(4-methoxyphenylethyl)-N-[(2-oxiranyl)-methyl]-methanesulfonic acid amide is added (Example 2g), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (eluent: chloroform/methanol; methanol: 0–80%).

Yield: 7.02 g (49.0%), colorless oil

Analysis: Relative to the anhydrous substance Cld: C 55.36 H 8.03 N 9.78 S 4.48 O 22.35 Fnd: C 55.17 H 7.89 N 9.45 S 4.32 O

EXAMPLE 9b

1-[3-(N-[2-(4-Methoxyphenyl)-ethyl]-mesylamino)-2-hydroxypropyl]-4,7,10-tris-(hydroxycarbonylmethyl)-1,4,7,10-tetraazacyclododecane 7.16 g (10 mmol) of the protected ligand produced under Example 9a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml, and the resulting solution of the ligand is chromatographed on silica gel RP-18 (eluent: methanol/water; methanol: 0–20%).

Yield: 2.22 g (35.2%), colorless oil

Analysis: Relative to the anhydrous substance Cld: C 51.33 H 7.18 N 11.09 S 5.08 O 25.33 Fnd: C 51.22 H 7.31 N 10.47 S 4.92 O

EXAMPLE 9c

1-[3-(N-[2-(4-Methoxyphenyl)-ethyl]-mesylamino)-2-hydroxypropyl]-4,7,10-tris-(carboxylatomethyl)-1,4,7,10-tetraazacyclododecane gadolinium complex 1.90 g (3 mmol) of the ligand produced under Example 9b is dissolved in 50 ml of water and mixed with 543.7 mg (1.5 mmol) of gadolinium(III) oxide. The resulting suspension is heated for 2 hours with vigorous stirring to 90° C., and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–40%).

Yield: 1.29 g (54.7%), white powder

Analysis: Relative to the anhydrous substance Cld: C 41.26 H 5.39 N 8.91 S 4.08 O 20.36 Gd 20.01 Fnd: C 41.03 H 5.57 N 8.73 S 3.82 O Gd 19.83

EXAMPLE 10a

1-{3-[N-(2-Benzyloxy-ethyl)-mesylamino]-2-hydroxypropyl}-4,7,10-tris-(ethoxycarbonylmethyl)-1,4,7,10-tetraazacyclododecane 200 ml of absolute ethanol is poured over 8.61 g (20 mmol) of N,N',N''-tris-(ethoxycarbonylmethyl)-1,4,7,10-tetraazacyclododecane (produced according to DE 36 25 417 A1) in a bomb tube. After 5.71 g (20 mmol) of N-[2-benzyloxy)-ethyl]-N-[(2-oxiranyl)-methyl]-methanesulfonic acid amide is added (Example 2h), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (eluent: chloroform/methanol; methanol: 0–80%).

Yield: 7.61 g (53.2%), colorless oil

Analysis: Relative to the anhydrous substance Cld: C 55.36 H 8.03 N 9.78 S 4.48 O 22.35 Fnd: C 55.09 H 7.78 N 9.50 S 4.19 O

EXAMPLE 10b

1-{3-[N-(2-Benzyloxy-ethyl)-mesylamino]-2-hydroxypropyl}-4,7,10-tris-(hydroxycarbonylmethyl)-1,4,7,10-tetraazacyclododecane 7.16 g (10 mmol) of the protected ligand produced under Example 10a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml, and the resulting solution of the ligand is chromatographed on silica gel RP-18 (eluent: methanol/water; methanol: 0–20%).

Yield: 2.12 g (33.6%), colorless oil

Analysis: Relative to the anhydrous substance Cld: C 51.33 H 7.18 N 11.09 S 5.08 O 25.33 Fnd: C 51.15 H 7.42 N 11.01 S 4.84 O

EXAMPLE 10c

1-{3-[N-(2-Benzyloxy-ethyl)-mesylamino]-2-hydroxypropyl}-4,7,10-tris-(carboxylatomethyl)-1,4,7,10-tetraazacyclododecane gadolinium complex 1.90 g (3 mmol) of the ligand produced under Example 10b is dissolved in 50 ml of water and mixed with 543.7 mg (1.5 mmol) of gadolinium(III) oxide. The resulting suspension is heated for 2 hours with vigorous stirring to 90° C., and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–40%).

Yield: 1.73 g (73.4%), white powder

Analysis: Relative to the anhydrous substance Cld: C 41.26 H 5.39 N 8.91 S 4.08 O 20.36 Gd 20.01 Fnd: C 40.98 H 5.63 N 8.82 S 3.85 O Gd 19.79

EXAMPLE 10d

1-{3-[N-(2-Hydroxy-ethyl)-mesylamino]-2-hydroxypropyl}-4,7,10-tris-(carboxylatomethyl)-1,4,7,10-tetraazacyclododecane gadolinium complex 1.57 g (2 mmol) of the complex produced under Example 10c is dissolved in 50 ml of water and mixed with 160 mg of palladium on carbon (10%). It is hydrogenated for 5 hours at room temperature and 1 atmosphere of hydrogen pressure. Then, it is filtered, concentrated by evaporation in a vacuum to about 10 ml and the complex is purified by chromatography on silica gel RP-18 (eluent: water/tetrahydrofuran; tetrahydrofuran; 0–40%).

Yield: 0.73 g (52.5%), white powder

Analysis: Cld: C 34.52 H 5.21 N 10.06 S 4.61 O 22.99 Gd 22.60 Fnd: C 34.38 H 5.39 N 9.81 S 4.32 O Gd 22.41

EXAMPLE 11a

1-{3-[N-2-Methoxyethyl-octadecylsulfamoyl)-2-hydroxypropyl}-4,7,10-tris-(ethoxycarbonylmethyl)-1,4,7,10-tetraazacyclododecane 200 ml of absolute ethanol is poured over 8.61 g (20 mmol) of N,N',N"-tris-(ethoxycarbonylmethyl)-1,4,7,10-tetraazacyclododecane (produced according to DE 36 25 417 A1) in a bomb tube. After 8.95 g (20 mmol) of N-[(2-methoxyethyl)-N-[(2-oxiranyl)-methyl]-octadecylsulfonic acid amide is added (Example 2), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (eluent: chloroform/methanol; methanol: 0–80%).

Yield: 9.32 g (53.1%), colorless oil

Analysis: Relative to the anhydrous substance Cld: C 60.17 H 9.99 N 7.97 S 3.65 O 18.22 Fnd: C 59.93 H 9.72 N 7.71 S 3.38 O

EXAMPLE 11b

1-{3-{N-2-Methoxyethyl-octadecylsulfamoyl)-2-hydroxypropyl}-4,7,10-tris-(hydroxycarbonylmethyl)-1,4,7,10-tetraazacyclododecane 8.78 g (10 mmol) of the protected ligand produced under Example 11a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml and the resulting solution of the ligand is chromatographed on silica gel RP-18 (eluent: methanol/water; methanol: 0–80%).

Yield: 2.93 g (36.9%), colorless oil

Analysis: Relative to the anhydrous substance Cld: C 57.48 H 9.52 N 8.82 S 4.04 O 20.15 Fnd: C 57.19 H 9.81 N 8.58 S 3.78 O

EXAMPLE 11c

1-{3-[N-2-Methoxyethyl-octadecylsulfamoyl)-2-hydroxypropyl}-4,7,10-tris-(carboxylatomethyl)-1,4,7,10-tetraazacyclododecane gadolinium complex 2.38 g (3 mmol) of the ligand produced under Example 11b is dissolved in 50 ml of water and mixed with 543.7 mg (1.5 mmol) of gadolinium(III) oxide. The resulting suspension is heated for 2 hours with vigorous stirring to 90° C., and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–60%).

Yield: 1.37 g (48.2%), white powder

Analysis: Relative to the anhydrous substance Cld: C 48.13 H 7.65 N 7.39 S 3.38 O 16.87 Gd 16.58 Fnd: C 47.94 H 7.87 N 7.18 S 3.16 O Gd 16.43 Relaxivity: in water 23.13 [l/mmol·s]; in plasma 27.57 [l/mmol·s]

EXAMPLE 12a

1-{3-[N-2-Methoxyethyl-toluenesulfamoyl)-2-hydroxypropyl}-4,7,10-tris-(ethoxycarbonylmethyl)-1,4,7,10-tetraazacyclododecane 200 ml of absolute ethanol is poured over 8.61 g (20 mmol) of N,N',N"-tris-(ethoxycarbonylmethyl)-1,4,7,10-tetraazacyclododecane (produced according to DE 36 25 417 A1) in a bomb tube. After 5.71 g (20 mmol) of N-[(2-methoxyethyl)-N-[(2-oxiranyl)-methyl]-toluenesulfonic acid amide is added (Example 2j), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (eluent: chloroform/methanol; methanol: 0–80%).

Yield: 6.17 g (43.1%), colorless oil

Analysis: Relative to the anhydrous substance Cld: C 55.36 H 8.03 N 9.78 S 4.48 O 22.35 Fnd: C 55.21 H 7.79 N 9.62 S 4.21 O

EXAMPLE 12b

1-{3-[N-2-Methoxyethyl-toluenesulfamoyl)-2-hydroxypropyl}-4,7,10-tris-(hydroxycarbonylmethyl)-1,4,7,10-tetraazacyclododecane 7.16 g (10 mmol) of the protected ligand produced under Example 12a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml, and the resulting solution of the ligand is chromatographed on silica gel RP-18 (eluent: methanol/water; methanol: 0–20%).

Yield: 3.18 g (50.3%), colorless oil

Analysis: Relative to the anhydrous substance Cld: C 51.33 H 7.18 N 11.09 S 5.08 O 25.33 Fnd: C 51.11 H 6.95 N 11.02 S 4.87 O

EXAMPLE 12c

1-{3-[N-2-Methoxyethyl-toluenesulfamoyl)-2-hydroxypropyl}-4,7,10-tris-(carboxylatomethyl)-1,4,7,10-tetraazacyclododecane gadolinium complex 1.90 g (3 mmol) of the ligand produced under Example 12b is dissolved in 50 ml of water and mixed with 543.7 mg (1.5 mmol) of gadolinium(III) oxide. The resulting suspension is heated for 2 hours with vigorous stirring to 90° C., and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–40%).

Yield: 1.03 g (43.7%), white powder

Analysis: Relative to the anhydrous substance Cld: C 41.26 H 5.39 N 8.91 S 4.08 O 20.36 Gd 20.01 Fnd: C 41.09 H 5.23 N 8.72 S 3.95 O Gd 19.78

EXAMPLE 13a

1-{3-[N-Octadecyl-octadecylsulfamoyl)-2-hydroxypropyl}-4,7,10-tris-(ethoxycarbonylmethyl)-1,4,7,10-tetraazacyclododecane 200 ml of absolute ethanol is poured over 8.61 g (20 mmol) of N,N',N''-tris-(ethoxycarbonylmethyl)-1,4,7,10-tetraazacyclododecane (produced according to DE 36 25 417 A1) in a bomb tube. After 14.84 g (20 mmol) of N-octadecyl-N-[(2-oxiranyl)-methyl]-octadecylsulfonic acid amide is added (Example 2k), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (eluent: chloroform/methanol; methanol: 0–80%).

Yield: 12.13 g (56.5%), colorless oil

Analysis: Relative to the anhydrous substance Cld: C 66.06 H 10.99 N 6.53 S 2.99 O 13.42 Fnd: C 65.89 H 10.72 N 6.52 S 2.81 O

EXAMPLE 13b

1-{3-[N-Octadecyl-octadecylsulfamoyl)-2-hydroxypropyl}-4,7,10-tris-(hydroxycarbonylmethyl)-1,4,7,10-tetraazacyclododecane 10.73 g (10 mmol) of the protected ligand produced under Example 13a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml, and the resulting solution of the ligand is chromatographed on silica gel RP-18 (eluent: methanol/water; methanol: 0–20%).

Yield: 2.97 g (30.04%), colorless oil

Analysis: Relative to the anhydrous substance Cld: C 64.40 H 10.71 N 7.08 S 3.24 O 14.57 Fnd: C 64.15 H 10.43 N 6.82 S 3.32 O

EXAMPLE 13c

1-{3-[N-Octadecyl-octadecylsulfamoyl)-2-hydroxypropyl}-4,7,10-tris-(carboxylatomethyl)-1,4,7,10-tetraazacyclododecane gadolinium complex 2.97 g (3 mmol) of the ligand produced under Example 13b is dissolved in 50 ml of water and mixed with 543.7 mg (1.5 mmol) of gadolinium(III) oxide. The resulting suspension is heated for 2 hours with vigorous stirring to 90° C., and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–70%).

Yield: 1.49 g (43.5%), white powder

Analysis: Relative to the anhydrous substance Cld: C 55.71 H 9.00 N 6.13 S 2.81 O 12.60 Gd 13.76 Fnd: C 55.47 H 9.21 N 5.98 S 2.54 O Gd 13.49

EXAMPLE 14a

1-{3-{N-[(3,3-Dimethyl-2,4-dioxa-cyclopentyl)-methyl]-mesylamino}-2-hydroxypropyl}-4,7,10-tris-(ethoxycarbonylmethyl)-1,4,7,10-tetraazacyclododecane 200 ml of absolute ethanol is poured over 8.61 g (20 mmol) of N,N',N''-tris-(ethoxycarbonylmethyl)-1,4,7,10-tetraazacyclododecane (produced according to DE 36 25 417 A1) in a bomb tube. After 5.31 g (20 mmol) of N-[(3,3-dimethyl-2,4-dioxa-cyclopentyl)-methyl]-methanesulfonic acid amide is added (Example 21), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (eluent: chloroform/methanol; methanol: 0–80%).

Yield: 7.33 g (52.7%), colorless oil

Analysis: Relative to the anhydrous substance Cld: C 51.78 H 8.26 N 10.06 S 4.61 O 25.29 Fnd: C 51.51 H 8.02 N 10.21 S 4.72 O

EXAMPLE 14b

1-{3-{N-[(3,3-Dimethyl-2,4-dioxa-cyclopentyl)-methyl]-mesylamino}-2-hydroxypropyl}-4,7,10-tris-(hydroxycarbonylmethyl)-1,4,7,10-tetraazacyclododecane 6.96 g (10 mmol) of the protected ligand produced under Example 14a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml and the resulting solution of the ligand is chromatographed on silica gel RP-18 (eluent: methanol/water; methanol: 0–20%).

Yield: 2.52 g (41.2%), colorless oil

Analysis: Relative to the anhydrous substance Cld: C 47.12 H 7.42 N 11.45 S 5.24 O 28.77 Fnd: C 46.91 H 7.71 N 11.18 S 5.02 O

EXAMPLE 14c

1-{3-[N-(2,3-Dihydroxypropyl)-mesylamino]-2-hydroxypropyl}-4,7,10-tris-(hydroxycarbonylmethyl)-1,4,7,10-tetraazacyclododecane gadolinium complex 2.45 g (3 mmol) of the ligand produced under Example 14b is dissolved in 50 ml of water and 50 ml of trifluoroacetic acid. The resulting reaction mixture is stirred for 4 hours at 60° C, the solvent is drawn off in a vacuum and the oily residue is dried in a fine vacuum. The resulting foamy oil is dissolved in 50 ml of water and the mixture is brought to pH 2.8 by adding ammonia water. After freeze-drying, it is dissolved in a little water and the ligand is purified by chromatography on silica gel RP-18 (eluent: water/methanol; methanol: 0–20%).

Yield: 1.29 g (56.2%), colorless oil

Analysis: Relative to the anhydrous substance Cld: C 44.12 H 7.23 N 12.25 S 5.61 O 30.79 Fnd: C 43.83 H 7.52 N 11.98 S 5.39 O

EXAMPLE 14d

1-{3-[N-(2,3-Dihydroxypropyl)-mesylamino]-2-hydroxypropyl}-4,7,10-tris-(carboxylatomethyl)-1,4,7,10-tetraazacyclododecane gadolinium complex 1.71 g (3 mmol) of the ligand produced under Example 14c is dissolved in 50 ml of water and mixed with 543.7 mg (1.5 mmol) of gadolinium(III) oxide. The resulting suspension is heated for 2 hours with vigorous stirring to 90 0C, and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–40%).

Yield: 0.95 g (43.6%), white powder

Analysis: Relative to the anhydrous substance Cld: C 34.75 H 5.28 N 9.65 S 4.42 O 24.25 Gd 21.66 Fnd: C 34.48 H 5.45 N 9.51 S 4.20 O Gd 21.37

EXAMPLE 15a

1-{3-[N-(3,5-Dioxa-4-phenyl-cyclohexyl)-mesylamino]-2-hydroxypropyl}-4,7,10-tris-(ethoxycarbonylmethyl)-1,4,7,10-tetraazacyclododecane 200 ml of absolute ethanol is poured over 8.61 g (20 mmol) of N,N',N''-tris-(ethoxycarbonylmethyl)-1,4,7,10-tetraazacyclododecane (produced according to DE 36 25 417 A1) in a bomb tube. After 6.27 g (20 mmol) of N-[(3,5-dioxa-4-phenyl-cyclohexyl)-methyl]-N-[(2-oxiranyl)-methyl]-methanesulfonic acid amide is added (Example 2m), the bomb tube is closed, flushed with nitrogen, and the resulting reaction mixture is heated for 16 hours to 90° C. After the reaction (TLC control) is completed, the solvent is evaporated in a vacuum and the yellowish, oily residue is chromatographed on silica gel (eluent: chloroform/methanol; methanol: 0–80%).

Yield: 7.74 g (52.0%), colorless oil

Analysis: Relative to the anhydrous substance Cld: C 54.89 H 7.72 N 9.41 S 4.31 O 23.66 Fnd: C 54.62 H 7.71 N 9.30 S 4.05 O

EXAMPLE 15b

1-{3-[N-(3,5-Dioxa-4-phenyl-cyclohexyl)-mesylamino]-2-hydroxypropyl}-4,7,10-tris-(hydroxycarbonylmethyl)-1,4,7,10-tetraazacyclododecane 7.44 g (10 mmol) of the protected ligand produced under Example 15a is dissolved in 350 ml of ethanol, mixed with 150 ml of 3N sodium hydroxide solution and stirred for 6 hours at 40° C. After saponification (TLC control) has taken place, it is concentrated by evaporation in a vacuum, taken up in 100 ml of water and mixed with enough 2N aqueous hydrochloric acid until the solution reaches pH 2.8. Then, it is concentrated by evaporation in a vacuum to a volume of 20 ml, and the resulting solution of the ligand is chromatographed on silica gel RP-18 (eluent: methanol/water; methanol: 0–20%).

Yield: 2.73 g (41.4%), colorless oil

Analysis: Relative to the anhydrous substance Cld: C 50.97 H 6.88 N 10.62 S 4.86 O 25.68 Fnd: C 50.72 H 6.97 N 10.38 S 4.61 O

EXAMPLE 15c

1-{3- [N-(1,3-Dihydroxyprop-2-yl)-mesylamino]-2-hydroxypropyl}-4,7,10-tris-(hydroxycarbonyl-methyl)-1,4,7,10-tetraazacyclododecane 1.98 g (3 mmol) of the ligand produced under Example 15b is dissolved in 50 ml of ethanol, mixed with 250 mg of palladium on carbon (10%) and then hydrogenated for 6 hours at room temperature and one atmosphere of hydrogen pressure. The resulting mixture is filtered, and the filtrate is released from the solvent in a vacuum. The residue is dissolved in water and chromatographed on silica gel RP-18 (eluent: water/methanol;

methanol: 0–20%).

Yield: 1.08 g (62.7%), colorless oil

Analysis: Relative to the anhydrous substance Cld: C 44.12 H 7.23 N 12.25 S 5.61 O 30.79 Fnd: C 44.01 H 7.51 N 12.03 S 5.42 O

EXAMPLE 15d

1-{3-[N-(1,3-Dihydroxyprop-2-yl)-mesylamino]-2-hydroxypropyl}-4,7,10-tris-(carboxylatomethyl)-1,4,7,10-tetraazacyclododecane gadolinium complex 1.71 g (3 mmol) of the ligand produced under Example 15c is dissolved in 50 ml of water and mixed with 543.7 mg (1.5 mmol) of gadolinium(III) oxide. The resulting suspension is heated for 2 hours with vigorous stirring to 90° C., and after the reaction (TLC control, clear solution) is completed, it is concentrated by evaporation on a rotary evaporator to a volume of about 10 ml. To purify the complex, it is chromatographed on silica gel RP-18 (eluent: water/tetrahydrofuran; tetrahydrofuran: 0–40%).

Yield: 0.93 g (42.7%), white powder

Analysis: Relative to the anhydrous substance Cld: C 34.75 H 5.28 N 9.65 S 4.42 O 24.25 Gd 21.66 Fnd: C 34.63 H 5.545 N 9.42 S 4.14 O Gd 21.53

| | Figure 1 | | |
|---|---|---|---|
| N-Substituted Sulfonic Acid Amide | Primary Amine | Sulfonic Acid Chloride | Yield |
| Ia N-Butyl-methanesulfonic acid amide | n-butylamine | methanesulfonic acid chloride | 95% |
| Ib N-octyl-methanesulfonic acid amide | n-octylamine | methanesulfonic acid chloride | 91% |
| Ic N-undecyl-methane-sulfonic acid amide | n-undecyl-amine | methanesulfonic acid chloride | 87.2% |
| Id N-(2-methoxy-ethyl)-methanesulfonic acid amide | 2-methoxy-ethylamine | methanesulfonic acid chloride | 90.9% |
| Ie N-benzyl-methane-sulfonic acid amide | benzylamine | methanesulfonic acid chloride | 91.2% |
| If N-(2-phenylethyl)-methanesulfonic acid amide | 2-phenyl-ethylamine | methanesulfonic acid chloride | 78.8% |
| Ig N-[2-(4-methoxyphenyl)-ethyl]ethanesulfonic acid amide | 2-(4-meth-oxy-phenyl)-ethylamine | methanesulfonic acid chloride | 89.4% |
| Ih N-(2-(benzyloxy)-ethyl)-methanesulfonic acid amide | 2-(benzyl-oxy)-ethylamine | methanesulfonic acid chloride | 92.9% |
| Ii N-(2-methoxy-ethyl)-octadecylsulfonic acid chloride | 2-methoxy-ethylamine | octadecylsulfonic acid chloride | 95.2% |
| Ij N-(2-methoxy-ethyl)-toluenesulfonic acid amide | 2-methoxy-ethylamine | tosyl chloride | 94.8% |
| Ik N-octadecyl-octadecyl-sulfonic acid amide | octadecyl-amine | octadecylsulfonic acid chloride | 91.7% |

Figure 2

| | N-Substituted N-((2-Oxiranyl)-methyl)-sulfonic Acid Amide | Yield |
|---|---|---|
| IIa | N-Butyl-N-((2-oxiranyl)-methyl)-methanesulfonic acid amide | 92.5% |
| IIb | N-octyl-N-((2-oxiranyl)-methyl)-methanesulfonic acid amide | 89.5% |
| IIc | N-undecyl-N-((2-oxiranyl)-methyl)-methanesulfonic acid amide | 91.3% |
| IId | N-(2-methoxy-ethyl)-N-((2-oxiranyl)-methyl)-methanesulfonic acid amide | 94.5% |
| IIe | N-benzyl-N-((2-oxiranyl)-methyl)-methanesulfonic acid amide | 89.9% |
| IIf | N-(2-phenyl-ethyl)-N-((2-oxiranyl)-methyl)-methanesulfonic acid amide | 92.3% |
| IIg | N-(2-(4-methoxyphenyl)-ethyl)-N-((2-oxiranyl)-methyl)-methanesulfonic acid amide | 90.4% |
| IIh | N-(2-(benzyloxy)-ethyl)-N-((2-oxiranyl)-methyl)-methanesulfonic acid amide | 87.5% |
| IIi | N-(2-methoxy-ethyl)-N-((2-oxiranyl)-methyl)-octadecylsulfonic acid amide | 95.2% |
| IIj | N-(2-methoxy-ethyl)-N-((2-oxiranyl)-methyl)-toluenesulfonic acid amide | 87.5% |
| IIk | N-octadecyl-N-((2-oxiranyl)-methyl)-octadecylsulfonic acid amide | 88.9% |
| IIl | N-((3,3-dimethyl-2,4-dioxa-cyclopentyl)-methyl-N((2-oxiranyl)-methyl)-methanesulfonic acid amide | 81.9% |
| IIm | N-((3,5-dioxa-4-phenyl-cyclohexyl)-methyl)-N-((2-oxiranyl)-methyl)-methanesulfonic acid amide | 79.7% |

We claim:

1. A 1,4,7,10-Tetraazacyclododecane compound of formula I

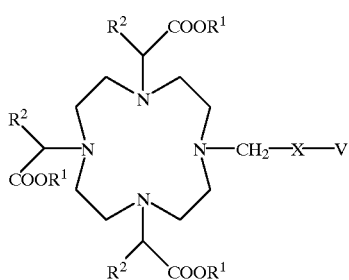

in which $R^1$, independently of one another, stand for H, a $C_1$–$C_6$ alkyl radical or a metal ion equivalent, $R^2$, independently of one another, stand for H, a methyl or ethyl radical, X stands for a direct bond or a $C_1$–$C_{10}$ alkylene group or a $C_2$–$C_{23}$ alkylene group interrupted by one or more oxygen atoms, whereby the alkyl radicals and alkylene groups are substituted optionally by one or more hydroxy radicals and/or lower alkoxy radicals and/or contain one or more carbonyl functions, and V means a radical of formula II

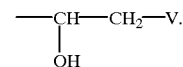

in which $R^3$ stands for a hydrogen atom, for a saturated, unsaturated, straight-chain or branched-chain alkyl, aryl or aralkyl radical or cyclic hydrocarbon radical with up to 40 carbon atoms, $R^4$ has the meaning indicated for $R^3$ with the exception of hydrogen or $R^3$ and $R^4$ together with the adjacent sulfur and nitrogen atoms represent a saturated 5- or 6-ring optionally containing another heteroatom, whereby $R^3$ and/or $R^4$ optionally have one or more carbonyl functions and/or are interrupted by one or more oxygen atoms and/or by one or more >N—$CH_2$-$COOR^1$ groups and/or are substituted by one or more O=C=N— or —S=C=N groups, or hydroxy, alkoxy, carboxylato, carbonyl, —CHO, halogen, amido or amino radicals, in which the hydroxy groups are present in free or protected form.

2. A compound according to claim 1, wherein X is a $C_2$–$C_5$ alkylene group and has at least one hydroxy radical.

3. A compound according to claim 2, wherein —X—V stands for a radical

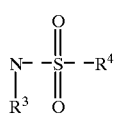

4. A compound according to claim 1, wherein at least two radicals $R^1$ stand for a metal ion equivalent of a metal of atomic numbers 21–29, 31, 32, 38, 39, 42–44, 49 or 57–83 and wherein optionally free carboxyl groups, i.e., not required for complexing the metal ion of the above-mentioned atomic numbers, are present as salt of an inorganic or organic base.

5. A compound according to claim 1, wherein it is linked with an amino acid, a peptide or other biomolecule or a polymer.

6. A pharmaceutical composition, containing at least one metal complex of general formula I of claim 1 with at least two radicals $R^1$ meaning a metal ion equivalent.

7. An agent for NMR diagnosis, diagnostic radiology or radiodiagnosis or radiotherapy, comprising a sulfonamide radical of formula II in an at least divalent metal complex compound or in a (chelate) compound, suitable for the production of an at least divalent metal complex compound

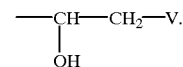

whereby $R^3$ stands for a hydrogen atom, for a saturated, unsaturated, straight-chain or branched-chain alkyl, aryl or aralkyl radical or cyclic hydrocarbon radical with up to 40 carbon atoms, $R^4$ has the meaning indicated for $R^3$ with the exception of hydrogen or $R^3$ and $R^4$ together with the adjacent sulfur and nitrogen atoms represent a saturated 5- or 6-ring optionally containing another heteroatom, whereby $R^3$ and/or $R^4$ optionally have one or more carbonyl functions and/or are interrupted by one or more oxygen atoms and/or by one or more >N—$CH_2$—$COOR^1$ groups and/or are substituted by one or more O=C=N—, S=C=N— groups or hydroxy, alkoxy, carboxylato, carbonyl, —CHO, halogen, amido or amino radicals.

8. A compound according to claim 7, wherein the sulfonamide radical is bound to a C atom of the complex compound.

9. A composition according to claim 8, wherein the complex compound is one of formula I of claim 1 in which at least two radicals $R^1$ mean a metal ion equivalent.

10. A process for the production of a pharmaceutical agent according to claim 6, wherein a metal complex of formula I dissolved or suspended in an aqueous medium is brought into a suitable form for enteral or parenteral administration.

11. A process for the production of a 1,4,7,10-tetraazacyclododecane derivative of formula I according to claim 1, wherein an N-substituted sulfonic acid amide of formula IIa

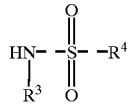
(IIa)

in which $R^3$ and $R^4$ have the meaning according to claim 1, is epoxyalkylated and the N-(epoxyalkyl)-sulfonic acid amide produced is reacted with a tetraazatricyclotridecane and the alkoxy radicals, optionally saponified with α-haloacetic ester, are alkylated, ester groups are cleaved off and finally metal ion equivalents are introduced.

12. A compound according to claim 2, wherein X has a hydroxy radical in β-position to the tetraazacyclododecane ring.

13. A compound according to claim 1, wherein $R^3$ is a hydrogen atom, a straight-chain or branched-chain $C_4$–$C_{18}$ alkyl radical, $CH_3$—O—$(CH_2)_2$—, $C_6H_5$—$CH_2$—, $C_6H_5$—$(CH_2)_2$—, $C_6H_5$—,—$CH_2$—O—$(CH_2)_2$—, $CH_3$—O—$C_6H_4$—$(CH_2)_2$—,

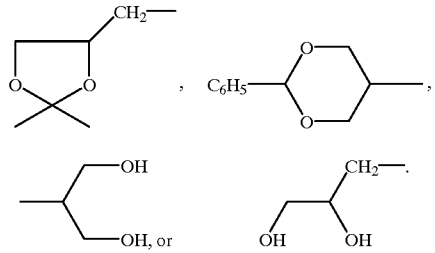

14. A compound according to claim 1, wherein $R^4$ is a straight-chain or branched $C_1$–$C_{18}$ alkyl radical or a $CH_3$—$C_6H_4$—, $C_6H_5$—, $O_2N$—$C_6H_4$—, $H_2N$—$C_6H_4$—, O=C=N—$C_6H_4$—, or S=C=N—$C_6H_4$ radical.

15. A compound according to claim 1, wherein $R^1$ is ⅓$Gd^{3+}$, $R^2$ is H, $R^3$ is $C_{1-16}$-alkyl or phenyl-$C_{1-4}$-alkyl and $R^4$ is $C_{1-6}$-alkyl.

16. In a method of NMR diagnosis, diagnostic radiology, radiodiagnosis or radiotherapy, the improvement comprising administering a compound of claim 1.

* * * * *